United States Patent [19]

Peschmann et al.

[11] Patent Number: 4,610,021
[45] Date of Patent: Sep. 2, 1986

[54] X-RAY TRANSMISSION SCANNING SYSTEM HAVING VARIABLE FAN BEAM GEOMETRY

[75] Inventors: Kristian R. Peschmann, San Francisco; John H. Bower, Palo Alto, both of Calif.

[73] Assignee: Imatron, Inc., South San Francisco, Calif.

[21] Appl. No.: 620,320

[22] Filed: Jun. 13, 1984

[51] Int. Cl.⁴ .............................................. G21K 1/04
[52] U.S. Cl. ...................................... 378/150; 378/152
[58] Field of Search .......................... 378/150, 10–12, 378/147, 152; 250/505.1

[56] References Cited

U.S. PATENT DOCUMENTS

| | | | |
|---|---|---|---|
| 4,137,455 | 1/1979 | Fetter | 378/10 |
| 4,158,142 | 6/1979 | Haimson | 378/10 |
| 4,277,687 | 7/1981 | Killig et al. | 378/147 |
| 4,323,783 | 4/1982 | Distler et al. | 378/4 |
| 4,347,624 | 8/1982 | Tschunt | 378/10 |
| 4,352,021 | 9/1982 | Boyd et al. | 378/10 |
| 4,361,902 | 11/1982 | Brandt et al. | 378/150 |
| 4,392,235 | 7/1983 | Houston | 378/10 |

Primary Examiner—Craig E. Church
Assistant Examiner—Charles F. Wieland
Attorney, Agent, or Firm—Flehr, Hohbach, Test, Albritton & Herbert

[57] ABSTRACT

A variable width fan beam of radiation is provided in a high speed X-ray transmission system by a plurality of ring collimators with the ring collimators being mounted whereby spacing between ring collimators can be varied. In preferred embodiment an arcuate array of radiation detectors are mounted in an annular housing which functions as one of the ring collimators.

4 Claims, 15 Drawing Figures

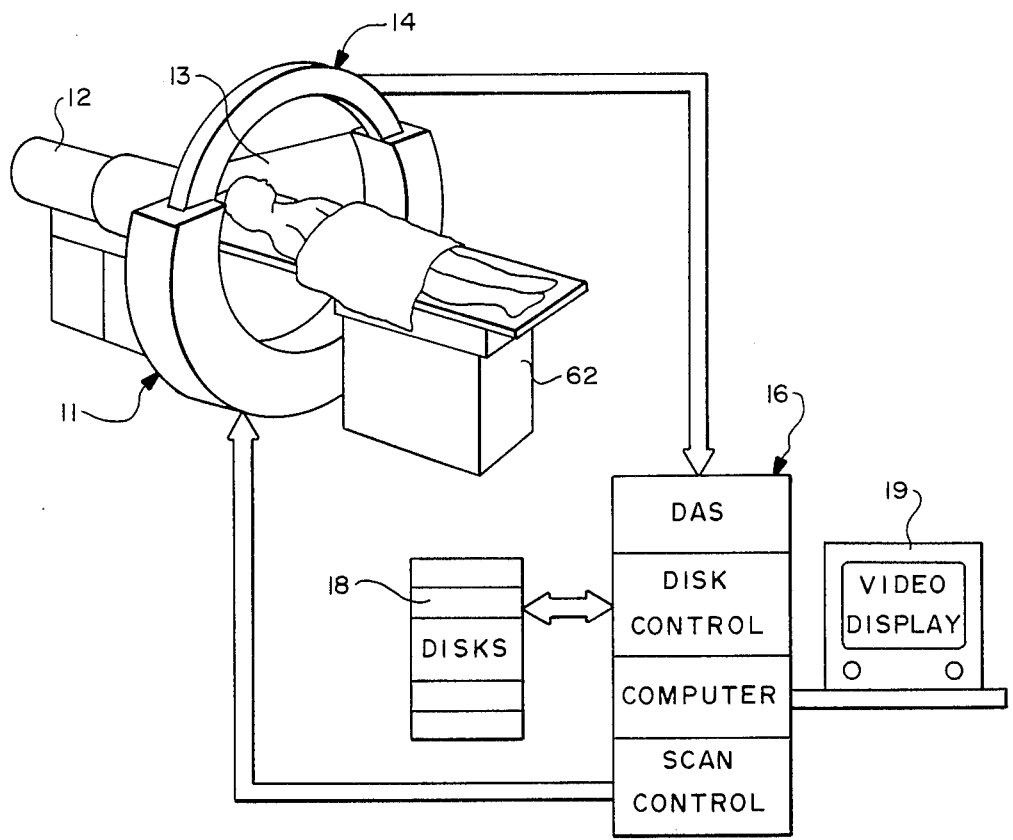
FIG.—1
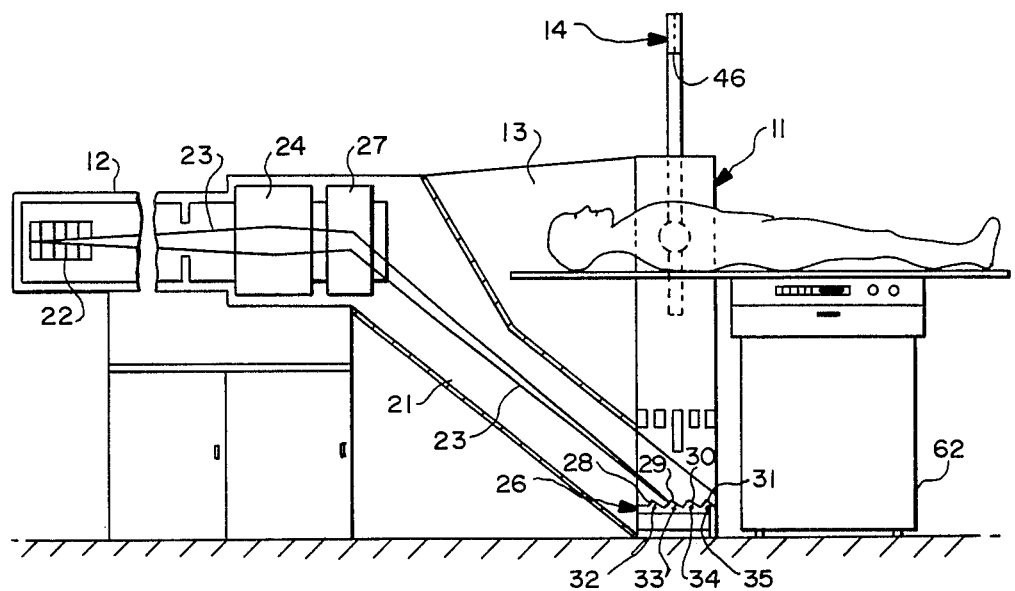
FIG.—2

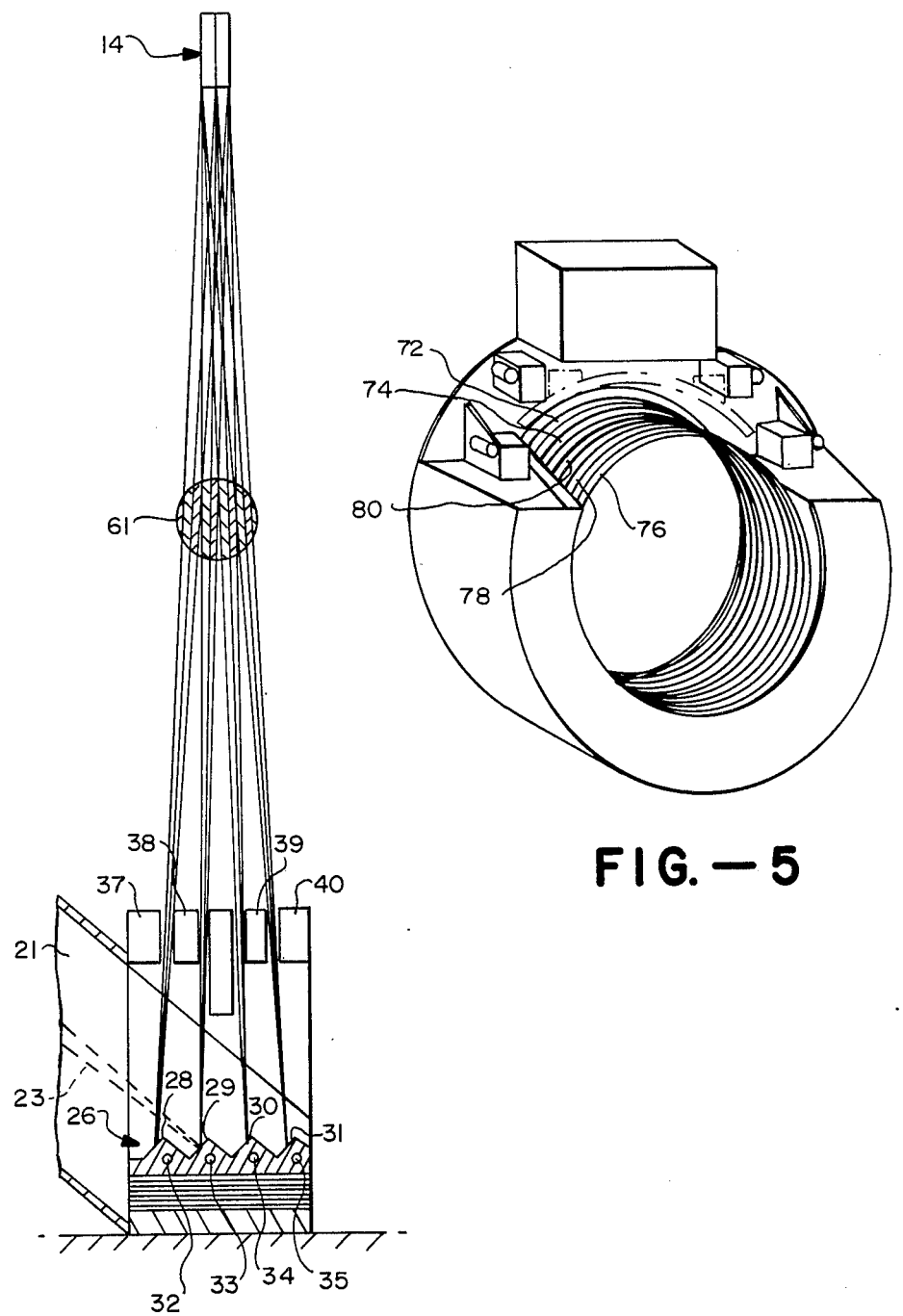

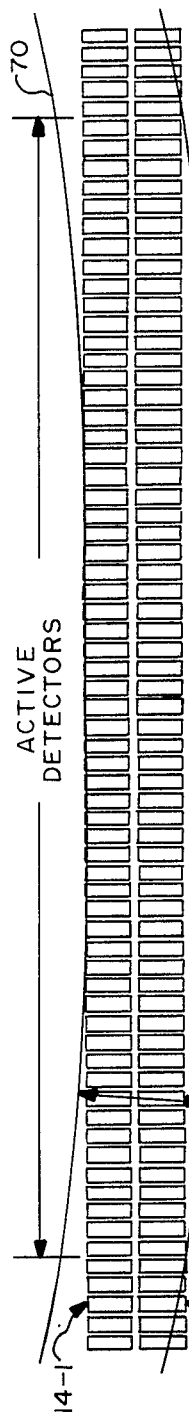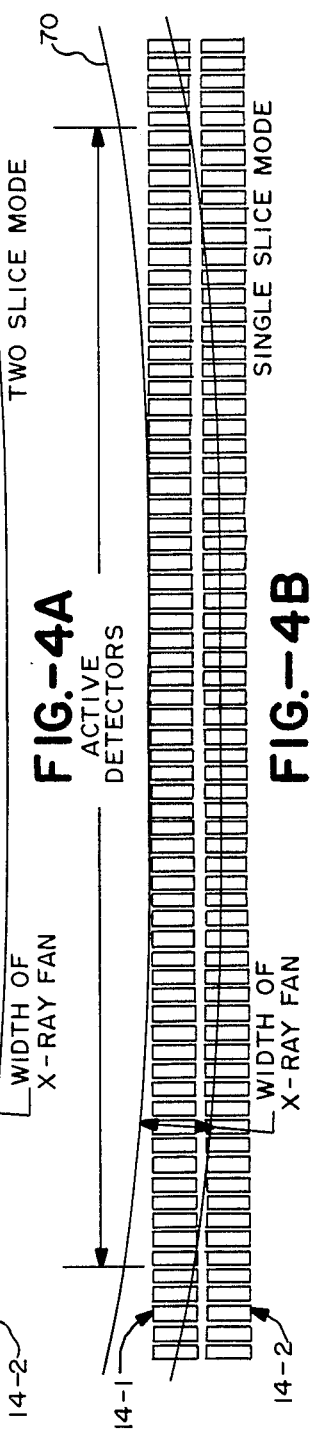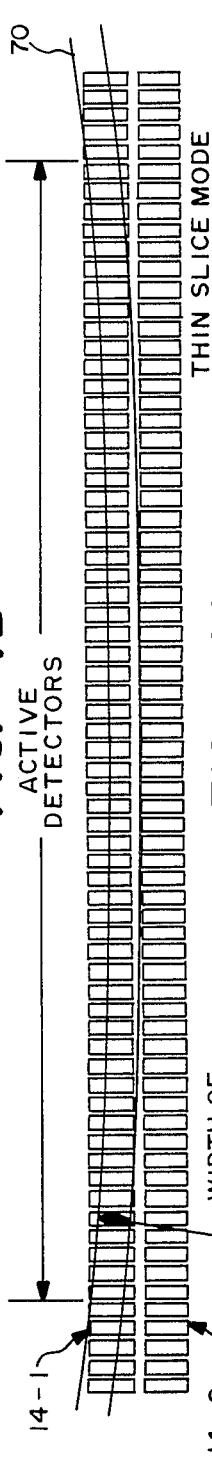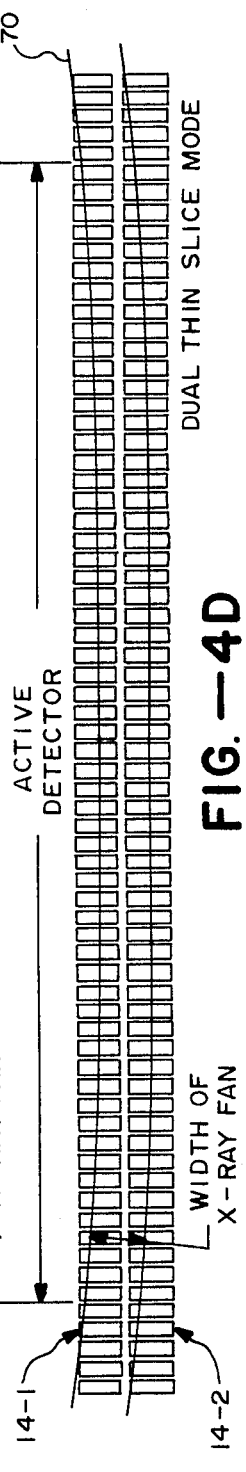

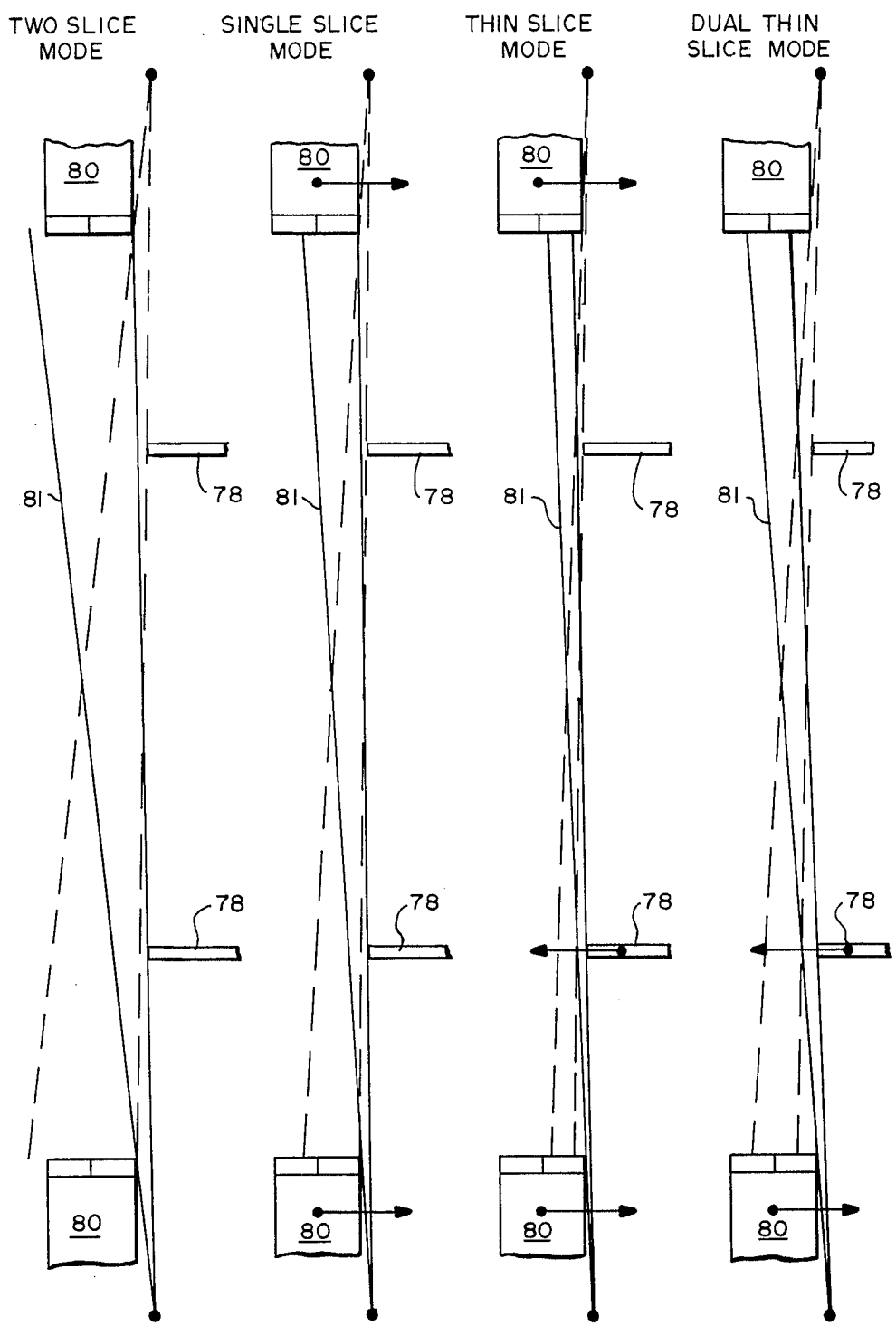
FIG.—6A  FIG.—6B  FIG.—6C  FIG.—6D

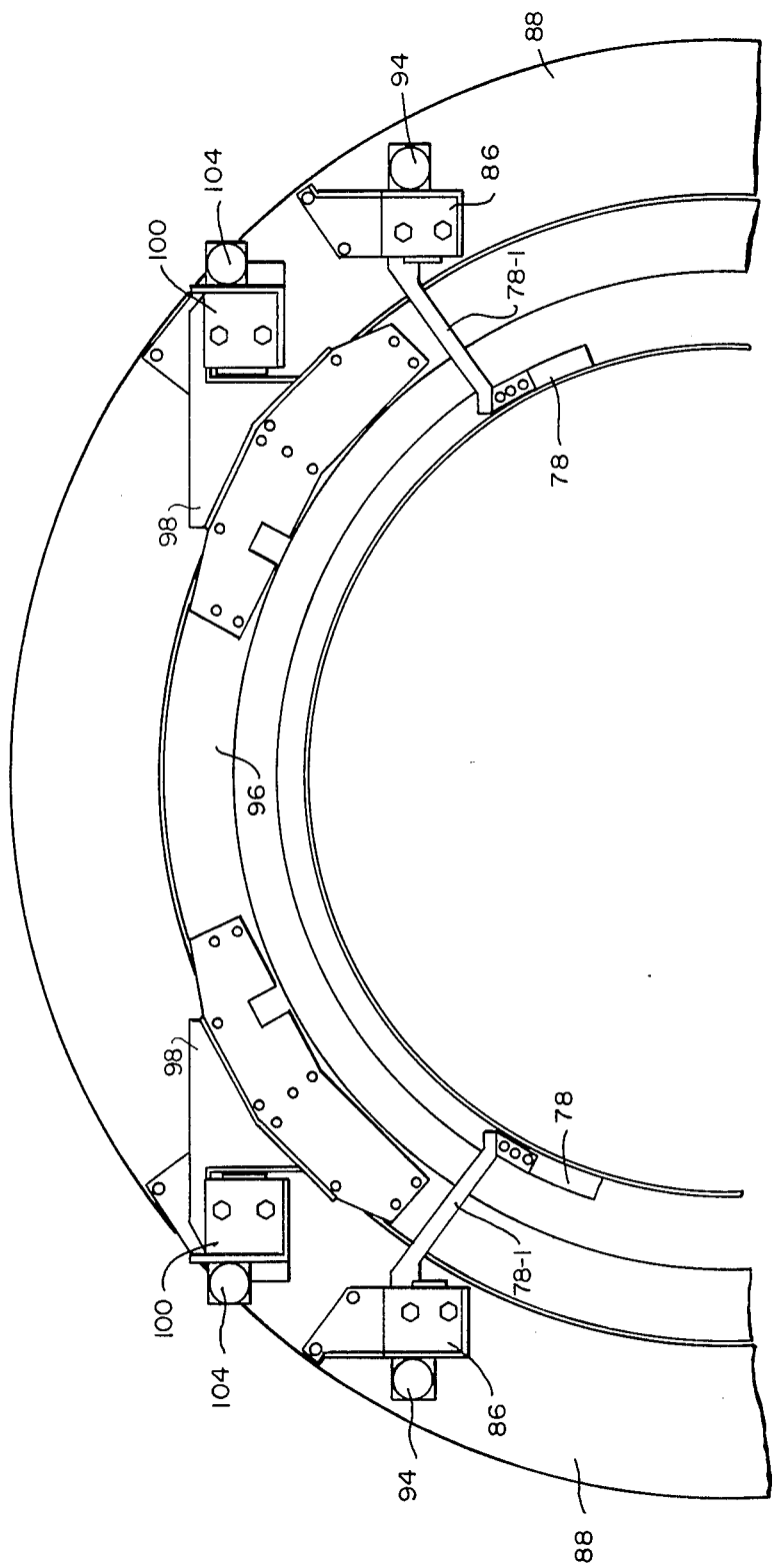
FIG.—7

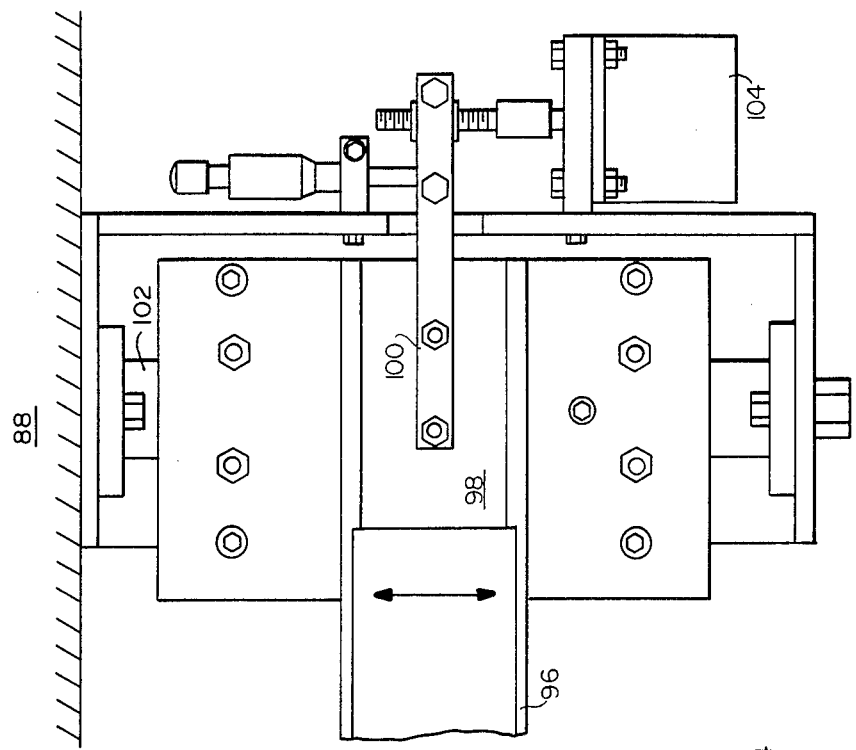
FIG.—9
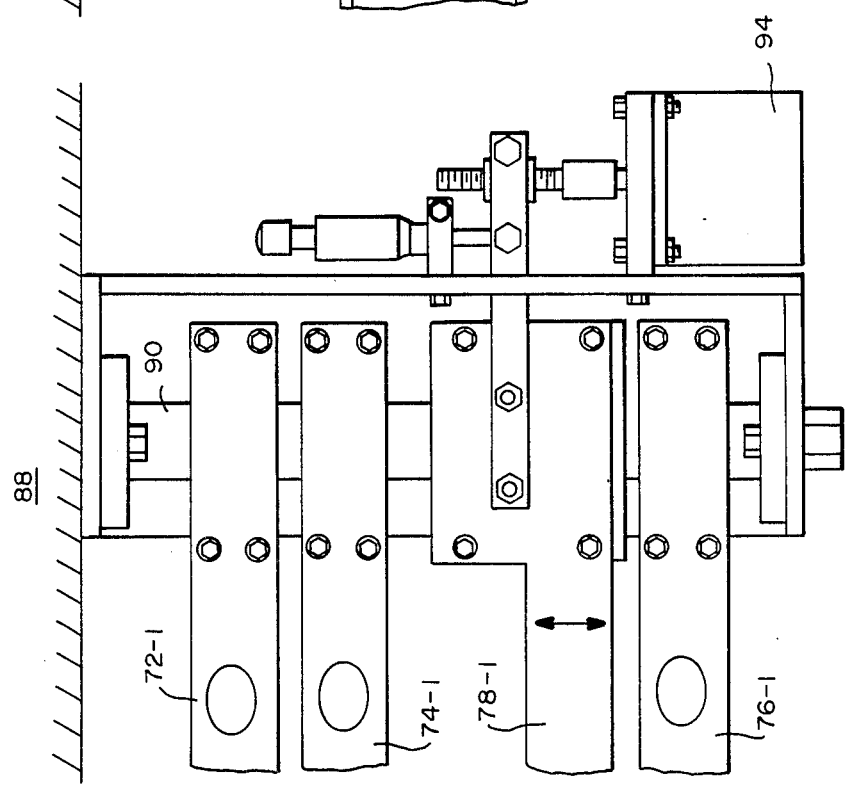
FIG.—8

X-RAY TRANSMISSION SCANNING SYSTEM HAVING VARIABLE FAN BEAM GEOMETRY

This invention relates generally to a high speed multiple section computed-tomographic (CT) medical scanning sytem, and more particularly the invention relates to an X-ray beam collimation structure for use therein.

Disclosed in U.S. Pat. No. 4,352,021 is a high speed X-ray scanning system in which the X-ray detectors are stationary and a plurality of fan beams of radiation is generated by sweeping an electron beam across a plurality of targets arcuately arranged whereby each target generates radiation fan beams. Such a system is now commercially available from Imatron, Inc., assignee of the present application.

The electronic scanning system incorporates a single electron beam tube. The electron beam is deflected by suitable magnetic and/or electric fields to produce a movable X-ray source on one of four adjacent partially circular target rings to provide scanning fan beams that can be used to image an entire volume of tissue in multiple sections. Such an electronic scanning system is vastly superior in speed to conventional mechanical scanning systems. Fraction-of-a-second scan time of a volume can be achieved as compared to one or more seconds required for the mechanial scan of a single section. The system eliminates the need for moving parts that require high precision and alignment. In addition, elaborate systems of sliding electrical contacts are eliminated. The scanner is an improvement over that shown and described in U.S. Pat. No. 4,158,142 in that it permits nearly simultaneous viewing multiple sections of the body which may encompass a region as large as the heart. The scanner can provide as many as eight sections.

The system employs a plurality of detectors mounted opposite the target rings. The detectors are arranged in two adjacent partial-circular ring arrays. Each of the arrays contains a multiplicity of detectors as, for example, 444 detectors each, providing a total of 888 detectors. The angular separation of two adjacent detectors is in the order of 0.5 degree resulting in very high resolution.

Although the basic scan geometry is complete by employing target rings for generation of a rotating X-ray focus and detector rings for intercepting and measuring the radiation attenuated by the object scanned, a collimation device is needed in order to (i) limit irradiation of and radiation dose to the scanned object to the required minimum and (ii) reduce the background of scattered radiation seen by the detector. Reduction of scattered radiation is required in order to get accurate measurements of attenuation and in order to limit extensive image noise introduced by the scattered radiation component.

Collimation can be provided by rings of finite width, made from x-ray opaque material, like thick brass or lead, and leaving gaps in between where the radiation is being transmitted freely. The radius of these collimator rings should be as small as possible but has to clear the required object aperture. Another constraint for the radius is that at those angular positions where parts of the target rings and the active detector rings are interleaved, the collimator rings do not obstruct the radiation leaving the object which has to be measured by the detector channels. The radius of the collimator hence cannot be made smaller than a certain value, which in case of a target radius of 90 cm, a detector radius of 67.5 cm and a distance of the target ring planes of 4.8 cm is 57.8 cm. With such arrangement, by running the electron beam subsequently on all four target rings and by measuring the attenuated radiation with a double ring of detectors, 8 levels can be scanned without moving the object/patient.

The described multi-section capability of the scanning device represents a clear advantage, when there is the requirement to image a volume completely in three dimensions in a very short time which does not allow to mechanically move the object scanned.

On the other hand, due to the offset of detector and target planes in this multi-level approach, each irradiated and imaged individual section volume takes on a complicated shape, slightly different from the ideal flat slice, and which could be described as a conical disk. Entailed is a slight inconsistency of the data measured. For most applications, this inconsistency does not cause significant problems, which is proven by the fact that other scanning systems in the field with mechanically moved x-ray pulses employ a similar geometry and deliver valuable diagnostic information.

However small the impact of the offset of detector and target planes of an eight level scanning device is on image quality, by applying the present invention the image quality of single level scans is improved. The present invention provides—for an eight level scanner—the option to perform as a single section scanner with reduced (multi-level) inconsistency of data, as mentioned above. Furthermore, the invention provides the option to scan single and dual thin sections. Furthermore, the invention makes possible a scan mode called tomoview wehre a large number of single level scans are obtained during movement of the scanned object through the scanned field. Furthermore—in all these scan modes—the invention keeps scattered radiation at a minimum which translates into keeping image noise at a minimum.

Accordingly, an object of the present invention is a high speed X-ray scanning system which has variable width fan beams and variable fan beam geometry.

A feature of the invention is support means for ring collimators which allows variable spacing of the collimators and thus variable widths and position of collimated fan beams of X-rays.

The invention and objects and features thereof will be more readily apparent from the following detailed description and appended claims when taken with the drawing, in which:

FIG. 1 is a schematic diagram partly in perspective showing a computed tomographic X-ray transmission scanning system employing multiple electron beam targets.

FIG. 2 is a cross section view of the system of FIG. 1.

FIG. 3 is an expanded cross sectional view showing the target rings, collimator rings, and the detector rings.

FIGS. 4A-4D illustrate four modes of operation of the system in accordance with the present invention.

FIG. 5 is a perspective view of the source collimator rings and detector ring with support means in accordance with one embodiment of the invention.

FIGS. 6A-6D illustrate positions of collimator rings and detector ring of FIG. 5 in obtaining the modes of operation of FIGS. 4A-4D.

FIG. 7 is a front elevation view of the source collimator rings and detector ring of FIG. 5.

FIG. 8 is a top view of a support means for the source collimator ring of FIGS. 5 and 6.

FIG. 9 is a top view of a support means for the detector ring in FIGS. 5 and 6.

Referring to FIG. 1, the system of U.S. Pat. No. 4,352,021 is seen to include three major components: a scan tube 11 including a cylindrical portion 12, and a semi-circular conical portion 13; a detector array 14; and, a computer system 16. The scan tube projects an electron beam to target rings which generate X-rays. The X-rays passed by detector collimator 46 are intercepted by the detector array 14. The output of the detector array is applied to the computer system 16. The computer system includes a plurality of storage discs 18 for recording the data for later processing. The computer system also includes an output which controls the scan tube. A video display 19 presents the data.

Referring more particularly to FIG. 2, the scanning system and detection system are shown in more detail. The electron beam tube 11 includes a vacuum envelope 21 which houses an electron gun 22 at the cylindrical end 12. The electron gun projects an axial electron beam 23 along the cylindrical portion. The focus coils 24 focus the beam onto targets 26. Bending coils 27 bend the beam so that it fans out along the partial-circular conical portion of the tube to impinge upon the partial-circular target rings. The target assembly 26 includes a plurality of partial-circular target rings 28, 29, 30 and 31. Suitable cooling coils 32, 33, 34 and 35 are associated with each of the target rings 28, 29, 30 and 31 respectively and serve to cool the target rings.

The bending magnets not only deflect the beam but rapidly sweep it along the partial-circular targets shown in FIGS. 2 and 3. The target rings are scanned serially to obtain a multiple section examination as will be presently described. Ring collimators 37, 38, 39 and 40 are disposed to intercept X-rays emitted by the target rings and define an X-ray beam projected as a one or two centimeter thick planar beam. A fanshaped sector of this beam is detected by the curved detector array and the measured values are utilized to reconstruct a tomographic image.

FIG. 3 shows the multiple section configuration where eight sections are being obtained by serial scanning of the four target rings in combination with the dual section detector ring 14. For each target sweep, a pair of normally one centimeter thick sections are scanned. A collection of eight sections covers a region of approximately eight centimeters indicated by the circle 61. This is sufficient to cover all of the left ventricle and most of the heart of a typical patient.

FIGS. 4A–4D are plan views of a portion of two detector arrays, 14-1 and 14-2, showing the one mode of operation in the presently available system and the three modes of operation in accordance with the present invention, respectively. In FIG. 4A the fan beam of radiation shown generally at 70 sweeps across the detector arrays in an arcuate manner due to the target rings and detector rings not being coplanar, as noted above. Thus, the active detectors are limited to the detectors of the arrays 14-1 and 14-2 which are fully illuminated by the fan beam sweep. In this eight section mode of operation two closely spaced fan beam slices are defined by the arrays 14-1 and 14-2.

Only the dual slice mode is presently available on the scanner. A single slice mode can be had but it is only achieved by not processing the information from one of the detector rings. The single slice mode illustrated shows a reduced width radiation fan. This is only achievable with the use of the invention (by readjusting the position of the detector ring and collimator ring). The advantage of a "single slice" as achieved using the invention is several fold:

(1) reduced radiation dose to patient (by about 50% reduction)
(2) reduced noise in the image as a result of the reduction of the radiation received and scattered by the patient.
(3) Data consistency and image quality improve because of reduced offset of target and detector planes.

Oftentimes it is desirable to define a thinner fan beam slice through a patient as illustrated in FIG. 4C and 6C. In this embodiment the X-ray fan covers less than the full width of a detector in the array 14-1. The provision of the variable width single slice mode of operation is permitted by the apparatus in accordance with the present invention.

FIG. 5 is a perspective view of the source collimator rings and detector ring with support means in accordance with one embodiment of the invention. In this embodiment three fixed collimator rings 72, 74 and 76 are provided and one movable collimator ring 78 is provided. In addition, the annular housing 80 for the detector array is movable. Thus, by moving the detector array housing (which acts as a collimator) and the movable collimator ring towards each other, the fan beam defined therebetween is reduced in thickness and position.

FIGS. 6A–6D illustrate the positions of collimator rings and detector ring in obtaining the modes of operation shown in FIGS. 4A–4D, respectively. The schematic cross section of FIG. 6 is taken at an orientation where detector and target rings—indicated by focal spots—are interleaved. The dashed lines indicate the collimated radiation fan boundaries after a 180° sweep of the x-ray focus. In FIG. 6A, collimator 78 and detector housing 80 provide a radiation beam 81 which irradiates the full width of the detector housing 80 and both rings of detectors therein. In FIG. 6B, the single level mode irradiates a single row of detectors in housing 80 and in FIG. 6D the single thin slice mode irradiates less than full width of a single row of detectors. In FIG. 6D the dual thin slice mode irradiates less than full width of both rows of detectors in housing 80.

FIG. 7 is a front view of the top portion of the collimator rings illustrating the mountings thereof, and FIG. 7 and FIG. 8 are top views illustrating the support structure for the collimator rings and the detector array, respectively. In FIG. 7 each collimator ring such as ring 78 is supported by means of a bracket 78-1 to the mounting structure 86 which is fastened to the system frame 88.

Referring to FIG. 8, the support structure 86 shows that the support brackets to the fixed rings (72-1, 74-1, 76-1) are fixed in position on a support rod 90 fastened to the frame 88. The support bracket 78-1 for the movable collimator ring 78 is slidably mounted on the rod 90 and is coupled to the stepper motors 94 which move the collimator ring 78 for the regular fan beam mode or the thin fan beam mode of operation.

Similarly, as shown in FIG. 7 and in FIG. 9, the detector ring 96 is attached by a bracket 98 to a support structure 100 mounted on the system of frame 88. The support structure 100 includes a support rod 102 on which the bracket 98 can move. Bracket 98 is coupled to a stepper motor 104 which moves the bracket 98 along support rod 102, and thus moves detector housing 96 towards or away from the movable collimator ring for the thin section mode of operation or the regular mode of operation, respectively.

Many CT scanners have adjustable slice thickness by adjusting the collimators. What makes the present invention different from other collimator designs is the fact that by moving the detector ring in conjunction with another collimator ring two things are achieved:

(1) the one edge of the X-ray fan is moved (which in conjunction with the other collimator ring narrows the slice thickness of the fan). Also as the edge moves, its curvature is substantially lessened, which is desirable (2) the detectors are simultaneously moved such that the X-ray fan remains centered favorably on the detecting elements or crystals. Other wise the ultimate thickness or thinness of the slice would be limited due to the curvature of the edges of the X-ray fan. Merely adjusting the collimators would not allow for a reduced slice thickness. This can be verified geometrically.

The X-ray scanning system and collimator structure in accordance with the invention provides greater flexibility in use of the high speed scanning system. While the invention has been described with reference to a specific embodiment, the description is illustrative of the invention and is not to be construed as limiting the invention. For example, a plurality of collimator rings can be moved rather than just one ring. Thus, various modifications and applications may occur to those skilled in the art without departing from the true spirit and scope of the invention as defined by the appended claims.

What is claimed is:

1. In an X-ray transmission scanning system in which X-rays are directed from an X-ray source to an arcuate array of detectors, X-ray collimation menas comprising a plurality of juxtaposed rings of X-ray impervious material for forming a plurality of fan beams, first support means for fixedly supporting at least one of said rings between said X-ray source and said array of detectors, and second support means for moveably supporting at least one other of said rings between said X-ray source and said array of detectors so that spacing between at least two rings can be varied for varying the thickness of a fan beam of radiation passing therethrough, said arcuate array of detectors being positioned in an annular housing, said annular housing forming one of said rings.

2. X-ray collimation means as defined by claim 1 wherein said first support means comprises a system frame, first and second rod means extending from said frame, first and second brackets attached to said at least one of said rings and to said first and second rod means, and said second support means comprising third and fourth brackets attached to said at least one other of said rings and to said first and second rod means.

3. X-ray collimation means as defined by claim 2 and further including motor means mounted to said system frame and attached to said second support means for variably positioning said at least one other of said rings.

4. X-ray collimation means as defined by claim 3 and including third and fourth rod means extending from said support system frame, fifth and sixth brackets attached to said annular housing and to said third and fourth rod means, and second motor means mounted to said system frame and coupled to said fifth and sixth brackets for positioning said annular housing on said third and fourth support rods.

* * * * *